(12) United States Patent
Delia

(10) Patent No.: US 8,620,448 B1
(45) Date of Patent: Dec. 31, 2013

(54) NON-INVASIVE, WIRELESS, PORTABLE DEVICE APPLICABLE TO THE FINGER TO REDUCE THE RISK OF SUDDEN INFANT DEATH SYNDROME AND REDUCE THE RISK OF APNEA, SLOWER HEART RATE, AND HEART ARREST IN ALL AGE GROUPS

(71) Applicant: Diego Alejandro Delia, Buenos Aires (AR)

(72) Inventor: Diego Alejandro Delia, Buenos Aires (AR)

(*) Notice: Subject to any disclaimer, the term of this patent is extended or adjusted under 35 U.S.C. 154(b) by 0 days.

(21) Appl. No.: 13/682,047

(22) Filed: Nov. 20, 2012

(51) Int. Cl.
  *A61N 1/18* (2006.01)
(52) U.S. Cl.
  USPC .......................................................... 607/62
(58) Field of Classification Search
  USPC .......................................................... 607/62
  See application file for complete search history.

(56) References Cited

U.S. PATENT DOCUMENTS

| | | | |
|---|---|---|---|
| 7,787,946 B2* | 8/2010 | Stahmann et al. | 607/3 |
| 7,789,837 B2 | 9/2010 | Lehrman et al. | |
| 8,308,641 B2* | 11/2012 | Moroney et al. | 600/301 |
| 2005/0027207 A1 | 2/2005 | Westbrook et al. | |
| 2008/0269832 A1 | 10/2008 | Wong et al. | |
| 2010/0099963 A1 | 4/2010 | Kilger | |

* cited by examiner

*Primary Examiner* — George Manuel
(74) *Attorney, Agent, or Firm* — Crowell & Moring LLP

(57) ABSTRACT

A non-invasive, wireless, portable device is applicable to the finger in order to reduce the risk of the sudden infant death syndrome and to reduce the risk of apnea, slower heart rate, and heart arrest in all age groups. The device is placed tightly on the distal end of a user's finger. As it is placed on the finger, this device may be inside a fabric cap attached to a glove of different sizes. This device measures blood oxygen saturation and heart rate through a sensor that is preferably a pulse oximeter. When any of these parameters falls below certain user-predetermined thresholds, an electric discharge is delivered to stimulate the user's reaction and a local and/or remote alarm is fired. In certain applications, the device is adequate to make the sleeping user react, and in others to prevent the user from falling asleep.

26 Claims, 6 Drawing Sheets

NON-INVASIVE, WIRELESS, PORTABLE DEVICE APPLICABLE TO THE FINGER TO REDUCE THE RISK OF SUDDEN INFANT DEATH SYNDROME AND REDUCE THE RISK OF APNEA, SLOWER HEART RATE, AND HEART ARREST IN ALL AGE GROUPS

The present invention refers to a non-invasive, wireless, portable device which is applied to a finger in order to reduce the risk of sudden infant death syndrome and reduce the risk of apnea, slower heart rate and cardiac arrest in all age groups.

APPLICATION FIELD OF THE DEVICE

The Sudden Infant Death Syndrome (SIDS) is defined as the sudden and unexpected death of an infant of less than 1 year who otherwise seems to be healthy. It is also known as "infantile sudden death syndrome," "cradle death," or "white death." The infant is generally found dead after having put him/her to bed, with no signs of having suffered any stress or health disorder. The present invention aims at early detecting a lack of oxygenation and forcing the user to react instantly in order to compensate the lack of oxygenation detected and also to generate an alarm signal before the infant dies, and if the double device is used, to send an alarm signal to the parent or tutor as well. It should be mentioned that for patients with this syndrome, the alarm signal may be set as soon as the heart rate and/or blood oxygen level fall.

The sleep apnea syndrome is the most frequent among respiratory disorders occurring during sleep, affecting around 4 percent of adults. Sleep apnea is a common disorder in which the affected person makes one or more pauses in respiration, or makes shallow respirations during sleep.

Pauses may last from a few seconds to several minutes. They usually may occur 30 or more times per hour. Respiration generally returns to normal, sometimes with a loud snore or choking sound.

Sleep apnea is almost always a chronic health condition altering sleep. The person goes from deep sleep to light sleep when there is a pause in respiration or when respiration becomes shallow.

For this reason, sleep gets insufficient and the person feels tired during the day. Sleep apnea is one of the main reasons why a person may feel very sleepy during the day. Sleep apnea goes usually undiagnosed. In general, physicians cannot detect it at ordinary visits to the health facility. In addition, there are no blood tests for detecting this problem.

Most people suffering from sleep apnea ignore their problem because it only occurs during sleep. The first one to note sleep apnea signs may be a family member or somebody sleeping in the same room as the affected person.

The most common type of sleep apnea is obstructive sleep apnea. Here, respiratory airways narrow or block during sleep, causing shallow respiration or pauses in respiration.

When the person tries to breathe, the air that manages to pass through the obstructed part may cause loud snoring. Obstructive sleep apnea is more frequent in overweight people, but may affect anyone. For example, small children with swollen tonsils may suffer from obstructive sleep apnea. Untreated sleep apnea may:
- Increase the risk of high blood pressure, heart attack, stroke (brain bleeding), obesity, and diabetes;
- Increase the risk of heart failure, or worsening of existing heart failure;
- Increase the chances of arrhythmias or irregular heartbeats;
- Increase the chances of suffering car or labor accidents.

Sleep apnea is a chronic health problem requiring long term treatment. Changes in lifestyle, buccal devices, surgery, or respiratory devices may be useful in the treatment of sleep apnea for many people.

When blood oxygenation is reduced (due to sleep apnea), patients with a heart condition, such as prior myocardial heart attack or chest angina, where there is stenosis in the arteries irrigating the heart, are more likely to suffer a new heart attack. This particularly important during airplane flights, where atmospheric pressure is lowered and so partial oxygen pressure in the blood is diminished. Usually, air pressure inside commercial airplanes is the same as the atmospheric pressure at an altitude of 2000-3000 meters, with a reduction in oxygen saturation between approximately 5 and 10 percent as compared to the normal level. The human body usually adapts to these situations, but it should be noted that if a patient with a certain heart or lung condition falls asleep and suffers from sleep apnea, the risk of complications is definitely higher. Therefore, when using the device of the present invention the number of heart attacks on airplanes can be reduced.

Detection of slower heart rate is of utmost importance, being an event that may occur in multiple situations, for example, in people driving transportation means that may feel tired at some point and whose heart rate may start to slow down until, in the most extreme cases, death occurs due to an accident happening because they fall asleep. It is important to point out that these people in a somnolence state prior to sleep suffer a reduction in their baseline heart rate.

The present invention is based on the use of a sensor measuring blood oxygen saturation and heart rate, and for this purpose, in a highly preferred embodiment, a pulse oximeter is employed.

The pulse oximeter is a medical device that indirectly measures oxygen saturation in the patient's blood, as opposed to the direct measurement of oxygen saturation on a blood sample, and it also measures the heart rate. The pulse oximeter is usually connected to a medical monitor so that the healthcare staff may check the patient's oxygenation and heart rate at all times. Those which are battery-operated are portable, allowing to measure oxygen saturation outside the hospital or on an outpatient basis.

The pulse oximeter is a highly convenient and non-invasive measuring device. It usually has two small light emitting diodes (LEDs) facing a photodiode through a translucent portion of the patient's body, generally a finger or toe, or an earlobe. One of the LEDs is red, with a wavelength of 660 nm, and the other is infrared, at 905, 910, or 940 nm. Absorption of these wavelengths is very different between oxyhemoglobin and its deoxygenated form, therefore, from the red/infrared light absorption ratio, the difference between oxyhemoglobin and deoxyhemoglobin may be calculated. Oxyhemoglobin and deoxyhemoglobin absorbance is the same (isosbestic point) at 590 and 805 nm; the first oximeters used these wavelengths for the correction of hemoglobin concentration. As mentioned before, another very important function of these sensors is to measure the patient's heart rate, which is also used in the present invention to detect a reduction in the heart rate and wake up the patient, and to prevent the sudden infant death syndrome. It is then worth mentioning that the present device may be used by people who are awake, since its design makes it totally portable.

BACKGROUND OF THE INVENTION

Various documents describing devices in the same technical field are known.

Document US 2010/0099963 A1 (Kilger) describes an apparatus and a method for monitoring a patient's blood oxygen content through a pulse oximeter 16 connected by a cable 25 to a device 50. This document explains that, if the oxygen content falls below a selected level, the apparatus delivers a peripheral nerve stimulation to the patient's wrist in the form of a milliamp current to arouse the patient through a wristband 18 that comprises electrodes 16 connected to the device 50 through a cable 15. Next, the apparatus delivers a signal to a remote monitoring system 42 and checks whether the patient has moved through a movement sensor 32 connected thereto by a third cable. If no patient movement has been detected, the apparatus increases the duration and/or intensity of the stimulus and repeats its application to the wristband 18, also sending a new signal to the remote monitoring system 42. This process is repeated until the movement sensor 32 detects the patient's movement. However, this apparatus has the great disadvantage that the patient's movement is not a dependable verification, and in fact, the wrong decision could be made since the only measurement that should be considered trustworthy is the blood oxygen level indicated by the pulse oximeter. The movement sensor in this apparatus adds cost, weight, and power consumption, especially if intended to be used as a portable equipment, and furthermore it introduces a potential source of failure in an apparatus that should provide maximum safety, as well as the existence of the 3 cables linking the apparatus with the oximeter, the wristband, and the movement sensor. Also, the apparatus does not process heart rate signals to make the decision to generate an electric discharge to the patient. Lastly, the use of a movement sensor does not make it adequate to be used as a portable device by the user who is not sleeping.

Document US 2008/0269832 (Wong et al.) discloses a device designed for fighting sleep apnea, comprising a pulse oximeter 101 located in the earlobe or a finger or toe, connected by means of a cable 103 or in a wireless way to the device 100, which is adapted to be attached around the patient's wrist in order to release electric pulses to two electrodes 113 applied on acupoints on the wrist (LU7) or alternatively on the arm and collarbone. The apparatus is portable and may be battery-operated or connected to a 220V AC power supply through a transformer. The document states that the oximeter 101 may be communicated to the device 100 by wireless Bluetooth®, infrared, or WIFI technology. When the patient's oxygen level falls below a certain level, the circuit releases a voltage pulse or series of pulses to force the patient's reaction. However, the device does not show the advantages of the present invention, since it does not use the heart rate measurement to activate a corrective action in the patient, nor may be used as a portable device when the patient is awake.

Document U.S. Pat. No. 7,789,837 describes an arrangement and method for interrupting obstructive sleep apnea before breathing stops. The arrangement 100 comprises a collar 145 including one or more microphones 125, 130, 135, and 140 to detect the sound of air passing through the patient's respiratory tract 120, which are connected to a control device. The microphone signals verify the patient's normal breathing and, when a respiratory anomaly takes place, for example apnea, the control device delivers an alarm signal to a base station 310 through radiofrequency. The document also mentions the existence of a movement sensor 360 on the patient's chest, sending alarm signals through radiofrequency to the base station if breathing stops. However, the device does not present the advantages of the present invention, since it does not use the heart rate measurement to activate a corrective action in the patient, nor may be used as a portable device when the patient is awake.

Document US 2005/0027207 A1 (Westrbrook et al.) describes a monitoring arrangement to collect and analyze physiological signs in order to detect sleep apnea, which is fixed to the patient's forehead and wherein pulse, blood oxygen values, snoring sounds, and head position are detected and stored. The monitoring arrangement may contain several sensors, such as a pulse oximeter, a microphone to detect snoring sounds, and a position sensor to detect the patient's head position. Although the document mentions that the oximeter delivers blood oxygen level signals and heart rate as well, it does not disclose nor suggest the activation of any stimulation signal for the patient to try to prevent occurrence of the abnormal health event, nor may be used as a portable device when the patient is awake.

Therefore, we conclude that none of the closest documents to the device in the present invention provides a portable apparatus that may be used by a user who is asleep or awake and carrying out normal activities.

DETAILED DESCRIPTION OF THE INVENTION

The present invention comprises a non-invasive, wireless, portable device that is placed on the distal end of a finger (see FIG. 4) and which measures blood oxygen saturation and heart rate by means of a pulse oximeter contained therein. In a first embodiment of this invention, in which patients use it when being asleep, as soon as any of these physiological parameters is detected to be out of a patient-predetermined range, the device releases a slight electric discharge on the finger, making the person change his position while sleeping and putting an end to the apnea episode or normalizing the heart rate. On the other hand, in a second usage embodiment in which patients use it while being awake, by reducing the heart rate, it releases an electric discharge and prevents them from falling asleep, which is extremely useful for drivers of any risky machinery and, particularly, any private or public transport means.

Figure 1:
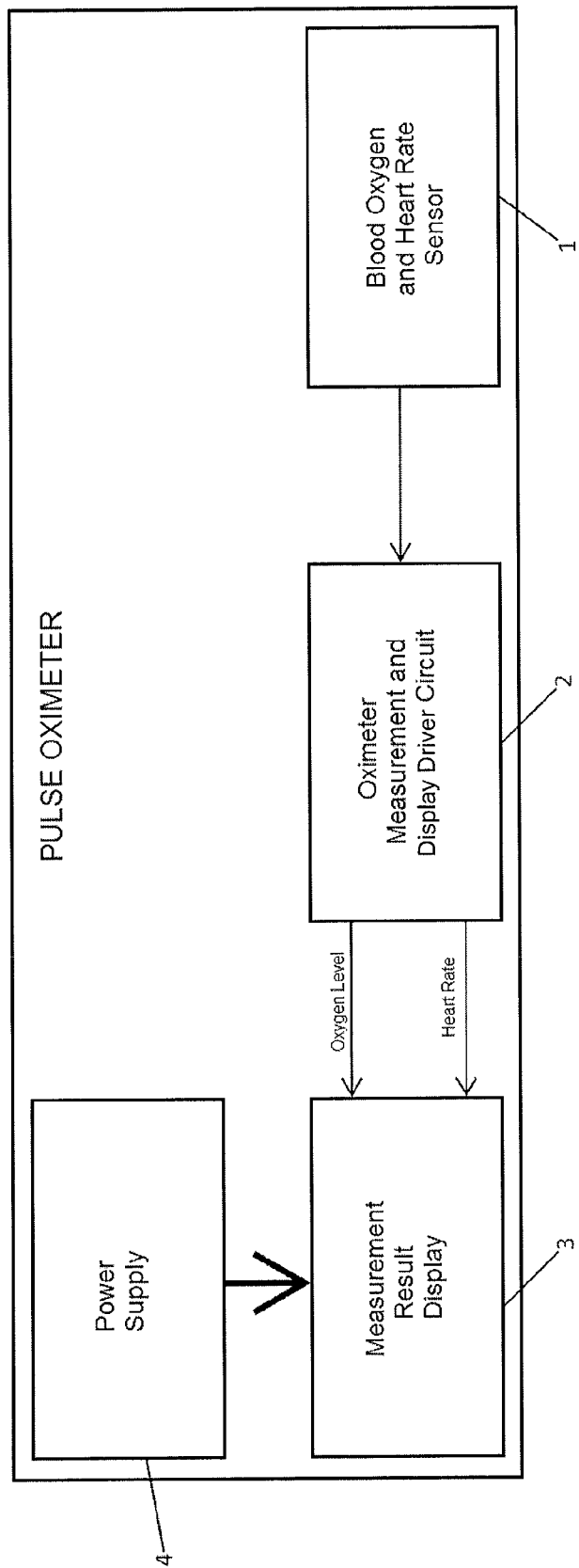
FIG. 1 is a basic block diagram of a typical portable pulse oximeter.

With reference to FIG. 1, a typical pulse oximeter is formed by a blood oxygen sensor 1 sending measurement signals to a measurement and display driver circuit 2. Circuit 2 contains the logic circuits that handle the measurement signals and sends the result to a display 3, which shows the resulting numeric values. The display shows the instant value for the blood oxygen content (measured as a percentage of the maximum value, e.g. 97-100% for a normal measurement) and heart rate (in beats per minute). The internal circuits of an oximeter are typically electrically supplied by a pair of alkaline or rechargeable batteries (generally AAA-sized or any other battery size appropriate for a portable apparatus).

Figure 2:
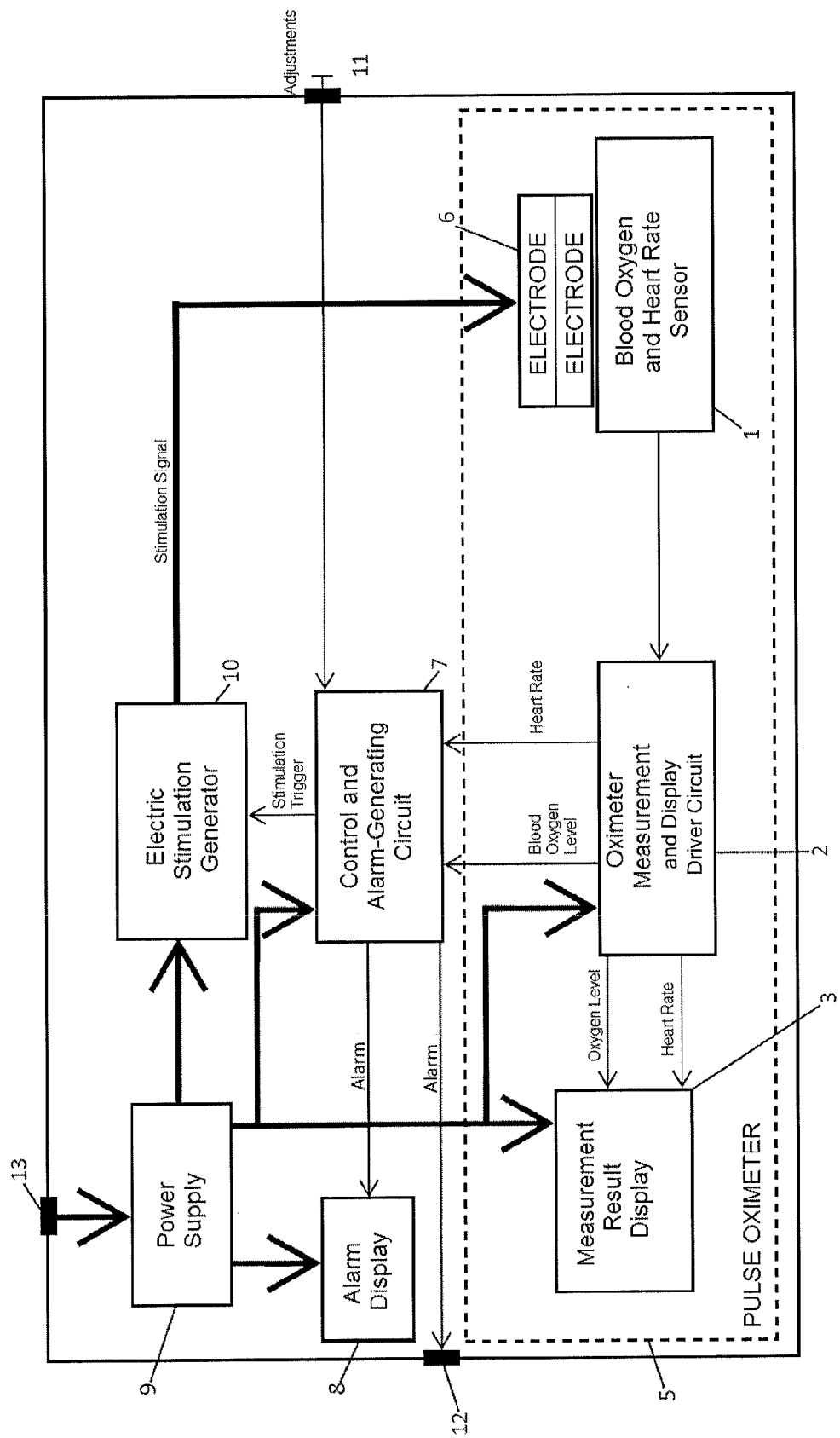
FIG. 2 is a block diagram of the device of the present invention.
Figure 3:
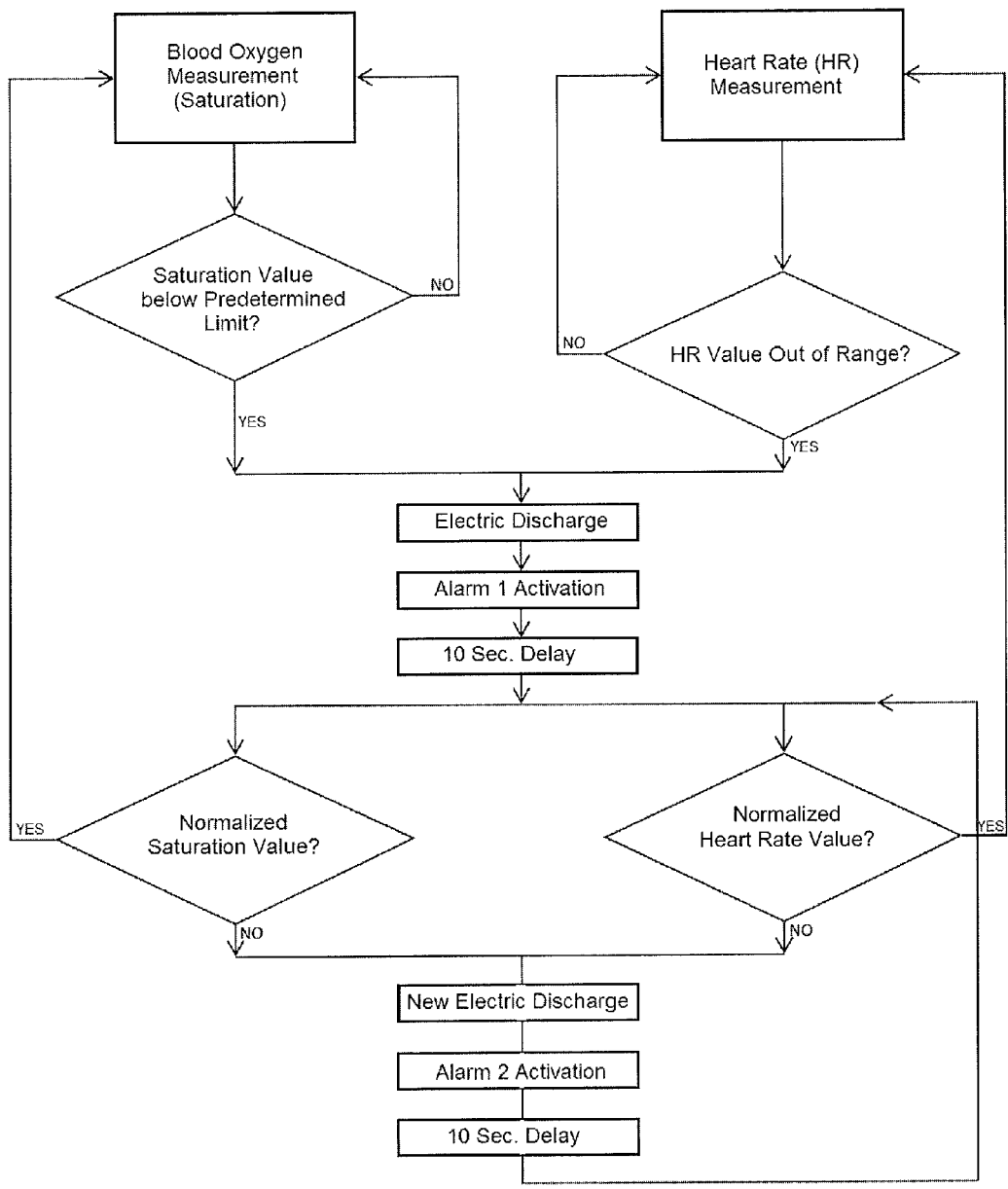
FIG. 3 is a flow chart of the steps taken by the device of the present invention.

With reference to FIG. 2, it may be see that the device is formed by the following elements, represented by schematic blocks: a block section 5 formed by almost all the typical elements that form a pulse oximeter, i.e., a blood oxygen saturation sensor and a heart rate meter 1, a measurement and display driver circuit 2, and a display 3 showing the numeric results. Also, block 5 has a pair of metal electrodes 6 physically arranged on both sides of sensor 1. The device also has a control and alarm-generating circuit 7, an alarm display 8, a power supply 9, and an electric stimulation generator 10, which will be further described in detail.

Block section 5 forming part of a pulse oximeter (blocks 1, 2, 3) are well known in the art and therefore will not be described in detail in this document. Display 3 may comprise a screen, a LED display, or any other technology appropriate for forming an alpha-numeric display. The present device receives the oxygen level signal, i.e., oxygen saturation, and the heart rate signal from the measurement circuit block 2 and connects them to a control and alarm-generating block 7. The control circuit 7 may consist of a pair of operational amplifiers that receive the signals and submit them to a feedback control loop with ON/OFF port, or else to an integrated circuit containing all these functions. The skilled in the art will understand that any other circuit technology may be used to solve these functions, either in a totally analog way or with analogical/digital conversion. The user may modify the threshold oxygenation and/or heart rate levels by pressing the push button 11 to adapt them to the requirements in each case. The control circuit will be adapted to modify its adjustment menu according to the signals received from the push button 11, in order to select the parameter to be adjusted with a single push button (for example, the adjustment parameter may be varied by pressing push button for a certain amount of time in order to determine the adjustment of the oxygen saturation threshold, and for another certain amount of time to adjust the heart rate threshold).

When the oxygen saturation sensor measures a level below the preset threshold, or if the heart rate falls below the preset threshold, the control circuit 7 will send a discharge order to the generator 10. In a simplified alternative embodiment, the block of control and alarm-generating circuit 7 and the block of electric stimulation generator 10 may be unified in a single integrated circuit designed for carrying out such effect.

When the driver of a means of transport falls into a state of sleepiness and suffers a reduction in his/her baseline heart rate, or while the user is sleeping, or if he/she suffers obstructive apnea at any time, the pulse oximeter detects a drop in blood oxygen saturation and/or a sudden drop in heart rate, which is seen in display 3, like in any typical pulse oximeter. At the time of an oxygen desaturation below a predetermined limit, or at the time of a drop in heart rate, a signal is triggered to the electric stimulation generator block 10, which delivers an electric stimulus to the finger skin through the two electrodes 6 placed on both sides of the sensor 1 detecting the oxygen saturation signal. The recommended threshold values are well known by the skilled in the health area; for example, the user may set a safety threshold of less than 92% for oxygen saturation, and a minimum heart rate of 50 beats/minute or 65 beats/minute for people that use it awake. In the event the user does not shift his/her position to improve oxygen saturation and/or to reestablish heart rate, another electric discharge of equal value is delivered after 10 seconds, and so on, until the airway obstructive episode and/or the cardiac episode ends. The device is provided with an optional outlet alarm connector 12 from which the discharge alarm can be remotely repeated through an optional cable which connects it to a safety monitoring apparatus. In an alternative low cost embodiment, the alarm display 8 may comprise a single LED that turns on to show an abnormal state or, in a more complete embodiment, through an alpha-numeric display indicating the occurrence of the abnormal state and further supplementary information, such as the type of problem, date and time of the alarm, etc.

The electric stimulation generator block 10 generates an electric sign that is weak enough so that the user's health is not compromised, but at the same time intense enough so as to make him/her react. The following table shows the effects of electric power on the human being.

| INTENSITY (mA) | | | | |
|---|---|---|---|---|
| DC | | AC (50 Hz) | | |
| MEN | WOMEN | MEN | WOMEN | EFFECTS ON THE BODY |
| 1 | 0.6 | 0.4 | 0.3 | No feeling |
| 5.2 | 3.5 | 1.1 | 0.7 | Perception threshold |
| 76 | 51 | 16 | 10.5 | Limit intensity threshold |
| 90 | 60 | 23 | 15 | Painful and serious shock (muscle contraction and difficulty in breathing) |
| 200 | 170 | 50 | 35 | Beginning of ventricular fibrillation |
| 1300 | 1300 | 1000 | 1000 | Possible ventricular fibrillation in short shocks: short duration (up to 0.03 seconds) |
| 500 | 500 | 100 | 100 | Possible ventricular fibrillation in short shocks: Duration 3 seconds |

Source: Universidad Politécnica de Valencia UPV—Servicio de Prevención de Riesgos Laborales de la UPV—Siemens SA División Productos Eléctricos (www.afinidadelectrica.com.ar/articulo.php?IdArticulo=90)

The values listed represent the current measured in mA, and it is therefore clear that the electric stimulus to be applied to the user should be between 3 and 10 mA DC, preferably between 3 and 7 mA.

Figure 4:
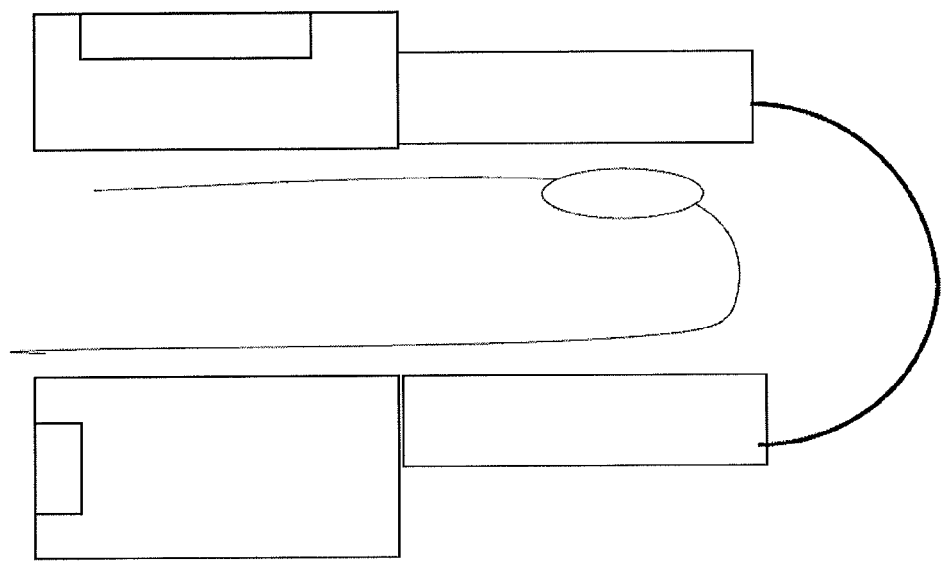
FIG. 4 is a side view of the device placed on the distal end of a patient's finger.

If the generator is designed so as to stimulate the user through DC voltage pulses, the number of volts allowing to obtain such values should be estimated. To apply Ohm's law, the approximate resistance value of the finger surface on which the device will be applied should be estimated. FIG. 4 shows that the device grabs the patient's finger from above and from below with a slight pressure, so as to ensure its contact with metal electrodes 6 and, in the case of very dry skin, some conductivity enhancing gel may be used. Electrodes 6 may be made of a good electricity-conducting metal, such as bronze, stainless steel, etc., and their size will depend on the miniaturization degree of the device, for example 0.6 cm×0.6 cm±20%.

The following table shows mean values of direct current resistance as a function of the current applied, measured in Ohms and obtained empirically from a population sample. A hand-to-hand path on dry skin is considered, using a measure sampling time=0.1 sec, through a contact surface: 100 cm².

| DC Current (Volts) | R (Ohms) 95% of the Population | R (Ohms) 50% of the Population | R (Ohms) 5% of the population |
|---|---|---|---|
| 25 | 2,200 | 3,875 | 8,800 |
| 50 | 1,750 | 2,990 | 5,300 |
| 75 | 1,510 | 2,470 | 4,000 |
| 100 | 1,340 | 2,070 | 3,400 |

-continued

| DC Current (Volts) | R (Ohms) 95% of the Population | R (Ohms) 50% of the Population | R (Ohms) 5% of the population |
|---|---|---|---|
| 125 | 1,230 | 1,750 | 3,000 |
| 220 | 1,000 | 1,350 | 2,125 |
| 700 | 750 | 1,100 | 1,550 |
| 1,000 | 700 | 1,050 | 1,500 |

Source: Seguridad eléctrica: efectos de la corriente eléctrica sobre el cuerpo humano—M. Villarrubia—Facultad de Física de la Universidad de Barcelona—(http://www.ing.unp.edu.ar/electronica/asignaturas/ee016/anexo/s-BIB851.pdf)

Next, a correction has to be applied to the resistance values considering the actual contact surface of the device electrodes which, as mentioned before, might be 0.6 cm×0.6 cm=0.36 cm²±5%, and the current path between them, which is an estimated finger thickness, might be approximately 1.5 cm separating both electrodes.

Assuming that the resulting resistance is inversely proportional to the contact surface and directly proportional to the distance between the electrodes, the resulting resistance of the electrodes in the invention for each current value would be:

$$R_e = R \times 100 \text{ cm}^2/0.36 \text{ cm}^2 \times 1.5 \text{ cm}/100 \text{ cm} = R \times 4.2$$

The resulting table for the pair of electrodes in the invention is as follows:

| DC Current (Volts) | $R_e$ (Ohms) 95% of the Population | $R_e$ (Ohms) 50% of the Population | $R_e$ (Ohms) 5% of the Population |
|---|---|---|---|
| 25 | 9,240 | 16,275 | 36,960 |
| 50 | 7,350 | 12,558 | 22,260 |
| 75 | 6,342 | 10,374 | 16,800 |
| 100 | 5,628 | 8,694 | 14,280 |
| 125 | 5,166 | 7,350 | 12,600 |
| 220 | 4,200 | 5,670 | 8,925 |
| 700 | 3,150 | 4,620 | 6,510 |
| 1,000 | 2,940 | 4,410 | 6,300 |

Conversion to current values is immediate through the well-known Ohm's formula: I(mA)=V (Volts)/R (Ohms)×1000 (adapting the units).

| DC Current (Volts) | I (mA) 95% of the Population | I (mA) 50% of the Population | I (mA) 5% of the population |
|---|---|---|---|
| 25 | 2.70 | 1.54 | 0.67 |
| 50 | 6.80 | 3.98 | 2.25 |
| 75 | 11.82 | 7.23 | 4.46 |
| 100 | 17.77 | 11.50 | 7.04 |
| 125 | 24.20 (*) | 17.00 | 9.92 |
| 220 | 52.40 (*) | 38.80 (*) | 24.65 (*) |
| 700 | 222.22 (*) | 151.51 (*) | 107.52 (*) |
| 1,000 | 34.01 (*) | 22.67 (*) | 158.73 (*) |

(*) Theoretical values that are dangerous for humans.

The resulting current values clearly indicate that the current pulses should be within the range of 25-50V DC if the pulse width is 0.1 sec. Further test have also shown that, with shorter application pulses, for example of 0.05 sec, the current could be within the range of 25-80V DC.

Then, in an embodiment of the invention, the discharge circuit 10 generates a low voltage pulse of 3V DC that is elevated to a voltage within the range of 25-50V DC through a pulse width modulation voltage booster, which charges a high voltage capacitor and applies pulse signals to the user, which may be in series, square waves, etc., with a frequency of 50 Hz and a width of around 0.1 ms for 1-5 seconds.

In a further alternative embodiment, the discharge circuit 10 generates a low voltage pulse of 3V DC that supplies a power supply circuit to apply current pulse signals to the user, in a range of 3 mA-10 mA and preferably of 3 mA-7 mA serial pulses, square wave pulses, etc., with a frequency of 50 Hz and a width of around 0.1 ms, for 1-5 seconds.

The user will be free to vary the current signal through the push button 11 in order to adapt it to the user's age, weight, and condition.

The power supply 9 provides stable direct current to all circuits in the device. In a preferred embodiment, with the aim of enhancing portability, the power supply is replaced by a receptacle holding a pair of alkaline or rechargeable batteries of 1.5V DC (AAA-sized). The device optionally has an alternative power input connector from an external 3V DC power supply in case the user does not have the batteries required. In a more developed embodiment, the power supply is a conventional regulated supply or, for a better miniaturization, a regulated switching power supply is used.

The electric discharge on the finger produces a slightly painful stimulus, and the user responds with an immediate increase of the heart rate. If this does not happen, the electric discharge will be repeated 10 seconds later, and so on.

Also, this device may be implemented in pairs, that is, a set of two devices interconnected by Bluetooth® or WIFI technology, which is ideal in cases in which the user is a newborn or infant, who must be communicated with his/her parent or tutor. In these cases, both devices receive the data of the child's heart rate and blood oxygen level and, therefore, in the event that any of these levels fall below normal, the electric discharge will affect both people.

Since the device was designed as a very small apparatus, it could easily fall off the user's finger. Hence, a glove in different sizes was designed, having a cap to contain the device inside while the user is sleeping. This cap is fixed to the glove with Velcro® (FIG. 7) and may be placed on any finger. The glove and the cap are made of elastic fabric and the cap has a transparent area made of plastic material, such as PVC or the like, to allow seeing the display on the device. The glove may vary according to the user's hand size. It should be mentioned that the cap designed for newborns or infants is especial: its end holds a rubber or silicone pacifier attached, which may be flavored, so that the child may suck it while wearing the device (FIG. 8).

Figure 5:
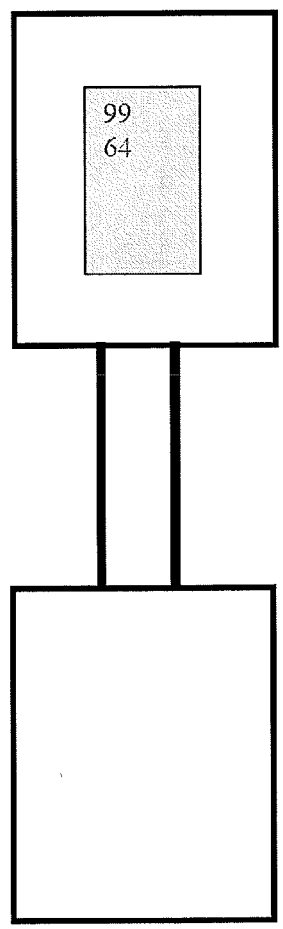
FIG. 5 is a top plan view of the external sides of the device completely open.

FIG. 5 shows a top plan view of the device alongside, where its external sides may be seen. One of them shows the display or LED screen, whose upper corner shows the blood oxygen level and whose lower corner shows the heart rate.

Figure 6:
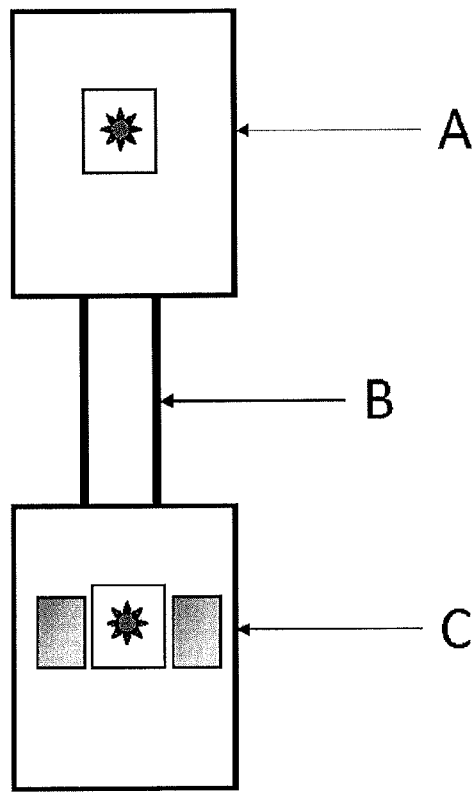
FIG. 6 is a top plan view of the internal sides of the device completely open.

FIG. 6 shows a top plan view of the device alongside, where its internal sides may be seen. One of them shows the oximeter infrared receptor, and on both sides, the metal electrodes releasing the electric discharge. The power supply, the control block, and the discharge block are contained in housing A. Housing C contains the oximeter elements and the electrodes on both sides of its sensor. Reference B shows the circuit connections between both housings.

Figure 7:
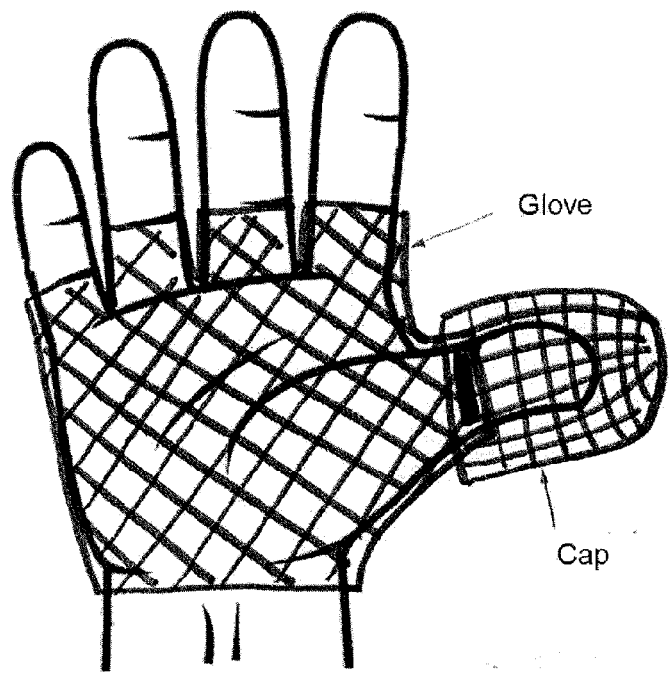
FIG. 7 shows the glove and cap designed to place the device on the patient's hand.
Figure 8:
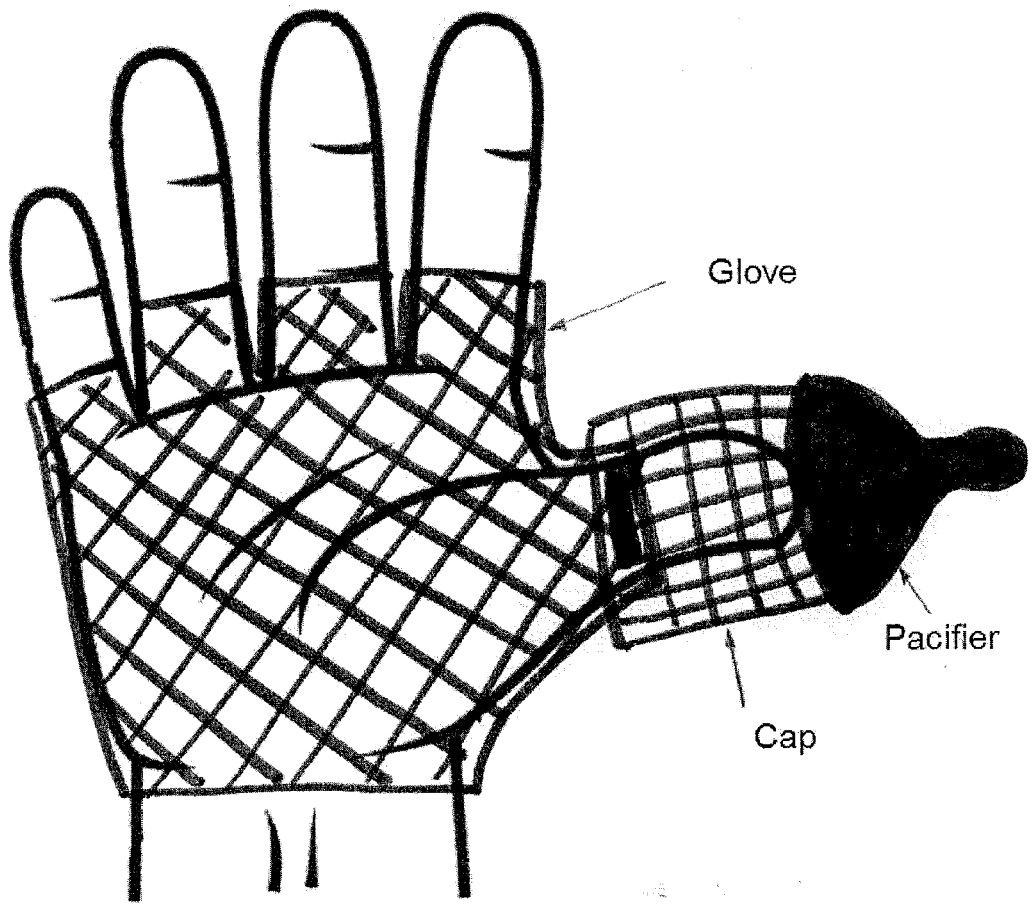
FIG. 8 shows the glove, cap, and pacifier especially designed to be used with the device.

FIG. 7 shows the glove and the cap adapted with Velcro® to the glove, containing the device of the present invention.

FIG. 8 shows the glove and cap adapted with Velcro® to the glove, containing the device of the present invention. It also shows the pacifier attached to the end of the cap. This design is ideal to be used by newborns and infants.

The device was designed for massive use, such as, for example, to be used by:
- people travelling by plane, who may use this device to reduce episodes of blood hypoxia, which may be under myocardial heart attack risk. Airlines could significantly reduce costs due to patients suffering from these diseases if they manage to make passengers use this device while on flight, when oxygen saturation usually diminishes due to reduced atmospheric pressure;
- all kinds of drivers, at the end of their workday or after long driving distances, when the heart rate may be reduced prior to falling asleep;
- bus drivers, especially long distance drivers, and lorry drivers as well. Transport companies can cut down costs for traffic accidents if their drivers use this device;
- train motormen, especially in middle and long distances;
- commercial airline pilots;
- hospitalized patients;
- surgical environments or post-anesthetics recovery rooms;
- people suffering from sleep obstructive apnea episodes who have failed with other methods;
- newborns and infants whose parents or tutors wish to feel safer through its use;
- nursing homes;
- couples in which one or both members snore;
- obese users;
- users with chronic obstructive pulmonary disease;
- users with a history of broncho-spasms;
- allergic users or those with a history of edema of glottis;
- relatives with a history of sudden infant death syndrome;
- users with various degrees of epilepsy;
- users with repeated vagal reflexes;
- users with panic attacks and other psychiatric conditions;
- users receiving sedatives or myorelaxing agents.
- users that suffer sleep apnea syndrome and were unable to receive satisfactory results with the others treatments.

I claim:

1. A non-invasive, wireless, portable device applicable to the finger in order to reduce the risk of sudden infant death syndrome and the risk of apnea, slower heart rate, and heart arrest in all age groups, comprising:
   a) a sensor (1) delivering blood oxygen saturation measurement signal and a heart rate measurement signal;
   b) a power supply (9);
   c) means (11) for setting threshold values for blood oxygen saturation and heart rate;
   d) a control and alarm-generating circuit (7), wherein said control and alarm-generating circuit (7) is designed to receive said blood oxygen saturation measurement signal to compare it with a blood oxygen saturation threshold value predefined by the user and generate a stimulation signal if said blood oxygen saturation signal falls below said blood oxygen saturation threshold;
   e) a pair of metal electrodes (6);
   f) an electric stimulation generator (10) designed to receive said stimulation signal from said control and alarm measurement circuit (7) and to generate an electric signal that is connected to said pair of electrodes (6) to apply a stimulus to the user when the blood oxygen saturation falls below said threshold;
   wherein:
   said control and alarm-generating circuit (7) is designed to also receive said heart rate measurement signal and compare it with a heart rate threshold value predefined by the user and generate said stimulation signal if said hear rate signal falls below said heart rate threshold.

2. The device according to claim 1, wherein said sensor (1) delivering a blood oxygen saturation measurement signal and a heart rate measurement signal is a pulse oximeter.

3. The device according to claim 2, wherein said oximeter section (5) further comprises a measurement and display driver circuit (2), and a display (3) for viewing measurement results.

4. The device according to claim 1, further comprising an alarm display (8).

5. The device according to claim 1, further comprising an alarm outlet connector (12) for remote monitoring.

6. The device according to claim 1, further comprising a Bluetooth® WIFI technology connection for communication with another similar device.

7. The device according to claim 1, wherein said adjustment means (11) comprises a programmable push button (11) to adjust oxygen saturation/heart rate thresholds and voltage/current discharge parameters.

8. The device according to claim 1, wherein said power supply section (9) comprises a battery support to house at least two alkaline or rechargeable batteries.

9. The device according to claim 1, wherein said power supply section (9) electrically supplies a regulated supply circuit.

10. The device according to claim 9, wherein said regulated supply is a conventional regulated power supply.

11. The device according to claim 9, wherein said regulated power supply is a switching power supply.

12. The device according to claim 1, wherein said power supply section (9) also comprises a connector (13) for receiving external power from an auxiliary power supply.

13. The device according to claim 1, wherein said control and alarm-generating circuit (7) and said electric stimulation signal generator circuit (10) are unified in a single circuit.

14. The device according to claim 1, further comprising an alarm signaling element (8).

15. The device according to claim 1, further comprising an alarm outlet connector (12) for remote monitoring.

16. The device according to claim 1, wherein said metal electrodes (6) are located on both sides of the blood oxygen sensor.

17. The device according to claim 1, wherein said metal electrodes (6) are approximately 0.6 cm×0.6 cm in size.

18. The device according to claim 1, wherein, after measuring and comparing the oxygen saturation and heart rate, the control and alarm-generating circuit (7) will apply a programmable waiting time before repeating the measurement and comparison.

19. The device according to claim 18, wherein said waiting time is 10 seconds.

20. The device according to claim 1, wherein said electric stimulation signal is a DC voltage pulse.

21. The device according to claim 20, wherein said electric stimulation signal comprises pulses with amplitudes within a range of 25-50V DC, with a pulse width of t=0.1 sec.

22. The device according to claim 20, wherein said electric stimulation signal comprises pulses within a range of 25-80V DC, with a pulse width of t=0.05 sec.

23. The device according to claim 1, wherein said electric stimulation signal is a DC current pulse.

24. The device according to claim 23, wherein said electric stimulation signal comprises pulses with amplitudes within a range of 3-7 mA.

25. The device according to claim 1, being contained inside a glove.

26. The device according to claim 25, being contained inside a cap which, in turn, is attached to said glove.

* * * * *